United States Patent [19]
Petrus

[11] Patent Number: 5,954,682
[45] Date of Patent: Sep. 21, 1999

[54] THERAPEUTIC APPLICATOR APPARATUS AND METHOD

[75] Inventor: Edward J. Petrus, Austin, Tex.

[73] Assignee: Advanced Medical Instruments, Austin, Tex.

[21] Appl. No.: 08/721,588

[22] Filed: Sep. 25, 1996

[51] Int. Cl.[6] .......................... A61M 35/00; A61F 13/20
[52] U.S. Cl. ................... 604/1; 604/11; 128/898
[58] Field of Search .................................. 604/1–3, 904, 604/11–18; 128/898

[56] References Cited

U.S. PATENT DOCUMENTS

| | | |
|---|---|---|
| 3,528,419 | 9/1970 | Joechle . |
| 4,034,759 | 7/1977 | Haerr . |
| 4,159,719 | 7/1979 | Haerr . |
| 4,278,664 | 7/1981 | Van Cleave . |
| 4,332,251 | 6/1982 | Thompson ............................... 604/904 |
| 4,938,959 | 7/1990 | Martin et al. . |
| 4,995,867 | 2/1991 | Zollinger . |
| 5,107,861 | 4/1992 | Narboni . |
| 5,417,224 | 5/1995 | Petrus et al. . |
| 5,476,446 | 12/1995 | Arenburg . |
| 5,641,503 | 6/1997 | Brown-skrobot ........................ 604/904 |

*Primary Examiner*—John G. Weiss
*Assistant Examiner*—Dennis Ruhl

[57] ABSTRACT

A therapeutic applicator comprises a porous media, a string attached to the porous media, and a hollow tube, having a first end and a second end. The string passes through the hollow tube and exits the hollow tube at the first end when the porous media is positioned in proximity of the second end. A therapeutic agent is impregnated in the porous media.

13 Claims, 2 Drawing Sheets

THERAPEUTIC APPLICATOR APPARATUS AND METHOD

BACKGROUND OF THE INVENTION

The invention relates generally to medical devices and, more particularly, relates to therapeutic applicator systems and methods locatable within body cavities.

Otitis media is a painful infection of the middle ear and ranks second only to the common cold as the most frequent illness among children in the United States. Acute otitis media is usually accompanied by fever, swelling, inflammation of the eardrum, and considerable pain. Otitis media develops when bacteria or viruses, usually associated with colds or sore throats, make their way up the eustachian tube, from the upper part of the throat behind the nose to the middle ear. As a result of the infection, the eardrum can become swollen and inflamed. When fluid accumulates against the eardrum, the condition is known as otitis media with effulsion or "glue ear." This condition can lead to hearing loss, and it may impair an affected child's learning and language skills.

Nearly 70% of U.S. children develop otitis media by age two. Because of the close anatomical relationship of the eustachian tube to the nasal cavity, otitis media is a frequent problem, especially in children in whom the tube is shorter, wider, and more horizontal than in adults. Many children outgrow their susceptibility to otitis media infection by age five. Over half of those children who experience acute otitis media have repeated episodes of the condition, and the condition may become chronic. Otitis media accounts for over 35% of all visits to pediatricians each year and represents more than $3.5 billion in U.S. health care costs annually.

Otitis media, with or without effusion, is also the most common reason antibiotics have been prescribed for children. The U.S. Food and Drug Administration (FDA) has found that about 14% of all courses of antibiotics prescribed in the United States are for otitis media. It has been shown that about 70% of ear infections have a bacterial etiology and 30% are viral in origin. Three types of bacteria, Streptococcus pneumoniae, Hemophilus influenza and Moraxella catarrhalis, cause 50% to 90% of middle ear infections. Many of these bacteria are now resistant to antibiotics. Furthermore, some children experience life threatening reactions to the antibiotics.

Conventional treatment for otitis media is implanting tubes in the eardrum to drain the middle ear, a surgical procedure known as tympanostomy. Tympanostomy is the most common surgery for otitis media. The surgical procedure requires administration of a general anesthetic and is typically performed on children under age two. In 1988, 800,000 children received 1.3 million tympanotomy tubes. Of these tubes, 30% were replacements. In 1986, 31 million visits to physicians were because of otitis media, and total direct and indirect costs for otitis media-related illnesses for that year have been estimated at $3.5 billion. Surgical costs, alone, for procedures for otitis media exceed $1.2 billion annually.

There are a number of risks of using ear tubes, including the following: risks associated with general anesthesia; tympanosclerosis occurs in about 51% of patients receiving ear tube implants; persistent otorrhea in 13% of ear tube patients; and an average 5-db hearing loss occurs to those receiving ear tubes. Beyond that, 30% of children receiving one set of tubes require a second set within five years of the first set. A study published in the Journal of the American Medical Association (JAMA), Apr. 27, 1994, found that 25% of tympanostomies were inappropriate. The study also found that, in about 30% of patients receiving tympanostomies, the benefits did not outweigh the risks of general anesthesia.

Another condition affecting the ear canal is otitis externa (commonly referred to as "swimmer's ear") which occurs in near-epidemic numbers during periods of hot, humid weather in which people spend time in swimming pools and enjoying aerobic exercises. Normally, cerumen (i.e., ear wax) and the acid pH of the external auditory canal protect the ear from infection. The canal can become infected, however, when the epithelium lining the canal becomes injured. This injury can occur through attempts to remove cerumen or entrapped water from the ear canal. In such instances, the epithelium can become macerated and susceptible to infection by Pseudomonas species, Staphylococcus aureus, and some fungi. The epithelium of the external auditory canal is tightly attached to the underlying bone or cartilage, and even a little swelling produces a great deal of pain in those affected. The macerated epithelial cells form a red and scaly dermatitis that may encroach on the epithelium of the tympanic membrane.

Otitis externa is treated by cleansing the canal with gentle curettage and irrigation and suction of the debris. Antibacterial, antifungal, or antiinflammatory medications, as well as drying-medications, are instilled into the ear canal. Fungal infections usually resolve when the acidic pH is restored. Acetic acid with steroids, or simply boric acid solution, alone, is generally adequate for immunocompetent patients. In diabetic or immunocompromised persons, however, otitis externa may progress to cellulitis of the scalp and osteomyelitis of the skull.

In conventional treatment of otitis externa, drying and medication is typically prescribed. A cellulose tampon (i.e., Pope ear wick) is sometimes inserted into the auditory canal and moistened with antibiotics to control the infection. Various drying-medications or steroids to relieve swelling may also be appropriate and may likewise be applied via the tampon or in other typical manners.

Certain conventional apparatus and methods provide for medicine application within body cavities, particularly the ear. For example, U.S. Pat. No. 5,417,224 to Petrus et al. discloses a tampon having loops through a spherical member for ease in removal from a body cavity. U.S. Pat. No. 3,528,419 to Joechle et al. discloses a resilient tampon impregnated with hormonal and steroidal preparations, which may be inserted into the auditory canal of domestic animals to affect reproductive physiology. U.S. Pat. No. 4,034,759 to Haerr discloses a hollow-cylindrical tube of cellulose material which may be inserted into the ear canal and which expands after the addition of medications. U.S. Pat. No. 4,159,719 also to Haerr discloses a tightly coiled moisture-expandable ear canal wick. U.S. Pat. No. 4,278,664 to Van Cleave discloses a preventative composition for the prevention of otitis externae. U.S. Pat. No. 4,938,959 to Martin et al. discloses a combination of an insoluble substance, such as nystatin, in powder or liquid form, mixed with soluble substances and applied to the ear canal. U.S. Pat. No. 4,995,867 to Zollinger discloses a syringe dispenser for the administration of medications to the ear canal. U.S. Pat. No. 5,107,861 to Narboni discloses an ear button for removing ear wax. Furthermore, U.S. Pat. No. 5,476,446 to Arenburg discloses a therapeutic treatment apparatus for use in the middle and inner ear for invasive microsurgical procedures.

Although the above-referenced patents address medicine application to body cavities, such as the ear, they do not provide for long-term, in-place treatment. Another disadvantage of the references is that the medicines and application mechanisms do not provide for easy removal from the body cavity.

What is needed, therefore, is a therapeutic applicator, and method of use thereof, which allows for long-term, in-place treatment of conditions within body cavities, such as the ear. Furthermore, easy removal of such a therapeutic applicator and method would be an added advantage and improvement.

SUMMARY OF THE INVENTION

An embodiment of the invention is a therapeutic applicator. The therapeutic applicator comprises a porous media, a string attached to the porous media, and a hollow tube, having a first end and a second end. The string passes through the hollow tube and exits the hollow tube at the first end when the porous media is positioned in proximity of the second end.

A further embodiment of the invention is a therapeutic applicator which comprises a porous media, and a string attached to the porous media.

Another embodiment is a method for applying treatment to a body cavity. The method for applying treatment to a body cavity comprises placing a porous media at an entry to the body cavity and pushing the porous media into the body cavity with a tube.

A further embodiment of the invention is a removal apparatus. The removal apparatus consists of a tube and a porous media adhered to the tube.

DETAILED DESCRIPTION OF THE PREFERRED EMBODIMENT

Figure 1:
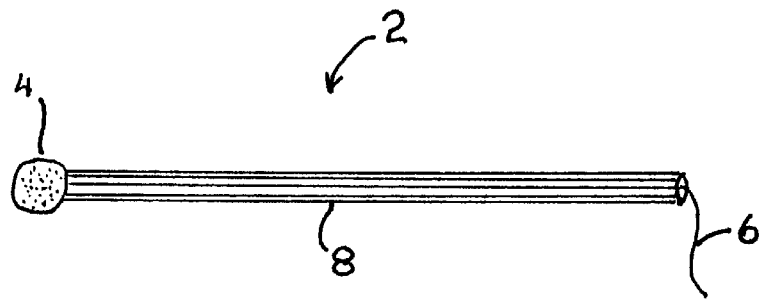
FIG. 1 shows a therapeutic applicator according to embodiments of the present invention.

Referring to FIG. 1, a therapeutic applicator 2 comprises a porous media 4. The porous media 4 is attached to a string 6. The string 6 is inserted through a hollow tube 8.

In certain embodiments of the therapeutic applicator 2, the porous media 4 is spherically-shaped. The diameter of the spherically-shaped porous media 4 may be on the order of the diameter of a body cavity within which the porous media 4 is to be inserted and maintained. In certain applications, the porous media 4 may be larger or smaller than the diameter of the body cavity. For example, certain types of the porous media 4 may swell upon application of medicine or other fluids thereto. A small diameter of porous media 4 may be appropriate in such instances in order that the body cavity may suitably accommodate the porous media 4.

The porous media 4 may be formed of a variety of materials, such as, for example, synthetic or natural sponge, cotton, or cloth, physiologically inert polymeric foam or polyurethane, polyether, polyester, or the like, or other synthetic or naturally occurring materials. In any event, the porous media 4 should have a porosity, for example, a fine porosity; should be pliable or compressible to conform to the body cavity and to allow for insertion and removal; should be sufficiently strong so as not to shred or disintegrate when located within the body cavity or when being removed from within the body cavity, and should adequately maintain attachment to the string 6 as hereinafter more fully discussed. If the porous media 4 is intended for location within an ear canal, the porous media 4 may be spherical and have a diameter of approximately the same diameter of the ear canal near the tympanic membrane, for example, on the order of about an 8–9 mm diameter, as is typical.

The string 6 may take a variety of forms and be a variety of materials. For example, a cotton, polyester, or other similar physiologically inert material may be used. The string 6 must be soft, yet sturdy and strong to withstand stress after long periods of immersion within and dampening by solutions. The string 6 may be a single strand or multiple strands. Also, the string 6 could be woven or knotted. The string 6 may even be a ribbon, tape, wire, filament, or some other similar cord. The string 6 is long enough to attach to the porous media 4 and to pass through and out of the hollow tube 8. A length on the order of about 50 mm to about 120 mm for the string 6 may be appropriate if the therapeutic applicator 2 is used for an inner ear canal, the typical length of such canal being on the order of about 24 mm.

The hollow tube 8, through which the string 6 passes, may be generally cylindrical and have longitudinal length. The hollow tube 8 should have an outer diameter on the order of less than the diameter of the body cavity into which the porous media 4 is to be inserted and maintained. The hollow tube 8 should have an inner diameter that is on the order of greater than the diameter of the string 6, so that the string 6 is freely moveable within the hollow tube 8 when inserted therein. The hollow tube 8 could alternatively be generally oval-shaped or have some other cross-sectional form.

In fact, the hollow tube 8 may, alternatively, have sides, internally or externally. For example, a triangular, square, pentagonal, or greater-sided tube may serve as the hollow tube 8. Furthermore, the hollow tube 8 may have sides of varying width, for example, the hollow tube 8 may be generally rectangular. The hollow tube 8, although shown in FIG. 1 as generally straight, can alternatively be curved or of some other shape. In any event, one consideration for the configuration of the hollow tube 8 is the dimensions and configuration of the body cavity into which the porous media 4 is to be inserted. Ease of entry and withdrawal of the hollow tube 8 into and from the body cavity may be an important characteristic of the hollow tube 8, and the hollow tube 8 should be configured and sized accordingly. In the case of a hollow tube 8 for use in a therapeutic applicator 2 for treating an ear canal, the hollow tube 8 may be on the order of about 50 mm to about 100 mm in length and may have an outer diameter on the order of about 4 mm to about 10 mm and an inner diameter on the order of about 0.5 mm to about 9 mm. In any event, the string 6, after attaching to the porous media 4, as hereafter described, extends through the length of the hollow tube 8 and exits with some portion of the string 6 remaining outside the hollow tube 8.

Figure 2:
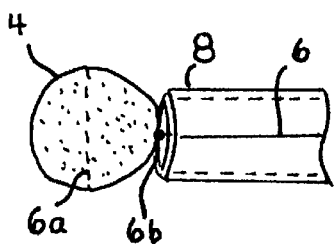
FIG. 2 shows a porous media of the therapeutic applicator, attached to a string, the string extending through a hollow tube, according to embodiments of the present invention.

Referring now to FIG. 2, in one embodiment, the porous media 4 is attached to the string 6 by placing the string 6 through the porous media 4 and tying a knot 6b to secure the porous media 4 by the string 6. A small hole (not shown in detail in the Figures) is formed in the porous media 4. The small hole may be formed through the diameter of the porous media 4. The small hole may be formed by drilling or can be molded as part of the porous media 4. The string 6 is fed through the small hole. Alternatively, a needle or similar puncturing device could be attached to the string 6 and threaded through the porous media 4, simultaneously creating the small hole and passing the string 6 therethrough.

Once passed through the small hole, the string 6 is tied in a knot 6b in order to retain the porous media 4 attached to the string 6. Several variations are possible for attaching the string 6 to the porous media 4. For example, the string 6 could be clasped, rather than knotted. Alternatively, some other attachment mechanism may be employed to attach the string 6 to the porous media, for example, an adhesive or melt weld could be used. Also, more than one string (not shown in the Figures) could be passed through the porous media 4 and the more than one string joined by knotting, clasping, or other attachment. The string is attached to the porous media in a manner such that when a tension force is applied to the string, the tension force is centered along the central longitudinal axis of the porous media.

Figure 3:
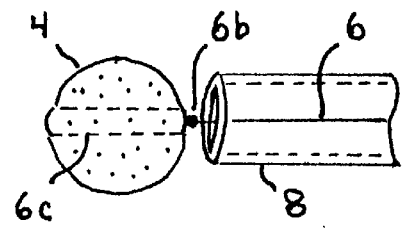
FIG. 3 shows a porous media of the therapeutic applicator, attached to the string, the string extending through a hollow tube, according to alternative embodiments of the present invention.

Referring to FIG. 3, in certain other embodiments, the porous media 4 is attached to the string 6 by passing the string 6 twice through the porous media 4. The string 6 passed twice through the porous media 4 is tied in the knot 6b in order to attach the string 6 to the porous media 4. The string 6 is fed through the hollow tube 8 as previously described. Of course, many variations in attaching the string 6 to the porous media 4 are possible, for example, the string 6 may be passed through the porous media 4 in other portions thereof, additional multiple passings of the string 6 through the porous media 4 are possible, and certain other variations may serve best under particular circumstances and uses.

Figure 4:
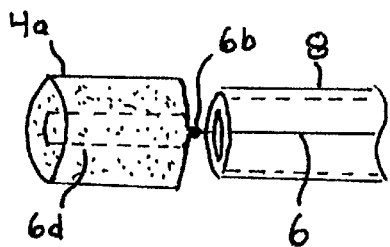
FIG. 4 shows a cylindrically-shaped porous media of the therapeutic applicator, attached to the string, the string extending through the hollow tube, according to alternative embodiments of the present invention.

Referring now to FIG. 4, in certain alternative embodiments, the porous media 4a may be cylindrical in shape. In those embodiments, the string 6 may be passed twice through the porous media 4a and then tied in the knot 6b to retain the porous media 4a attached to the string 6.

Figure 5:
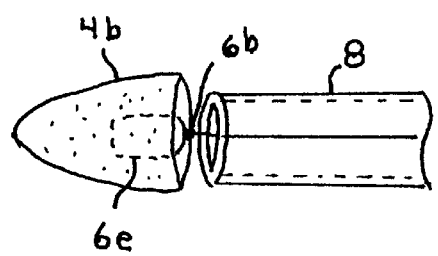
FIG. 5 shows a conically-shaped porous media of the therapeutic applicator, attached to the string, the string extending through the hollow tube, according to alternative embodiments of the present invention.

Referring to FIG. 5, in other embodiments, the porous media 4b is conically-shaped. The string 6 is looped within the body of the porous media 4b and the knot 6b secures the string 6 to the porous media 4b.

Figure 6:
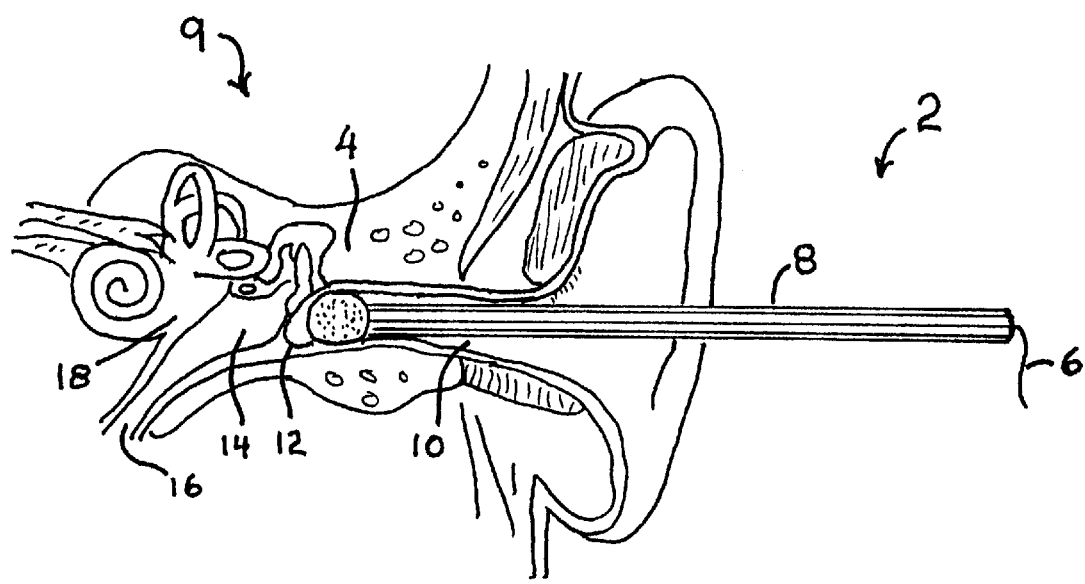
FIG. 6 is a cross-sectional view of portions of a human ear and the therapeutic applicator in use therewith to locate the porous media in the external ear canal near the tympanic membrane.

Referring to FIG. 6, in operation of the therapeutic applicator, the porous media 4 is located at a proximal end (i.e., the part closest to the midline of the head) of the external auditory canal 10 of an ear 9. The porous media 4 is inserted into the canal 10 with the help of the hollow tube 8. The string 6 extends from attachment to the porous media 4, through the hollow tube 8, to exit the hollow tube 8. A person grasps the hollow tube 8 and pushes the porous media 4 into the canal 10 by pushing the hollow tube 8 into the canal 10. The porous media 4, via the hollow tube 8, is pushed into the canal 10 until located at a select position therein. After the porous media 4 is so positioned, for example, against the tympanic membrane (ear drum) 12 at the end of the external auditory canal 10, as shown in FIG. 6, the hollow tube 8 is withdrawn from the canal 10. The porous media 4 remains within the canal 10. The string 6 remains attached to the porous media 4 and exits to outside the canal.

After the hollow tube 8 is so removed and the string 6 extends out the canal 10 to outside the ear 9, external portions of the string 6 are snipped, leaving only a remaining section of the string 6 within the canal 10. The remaining section of the string 6 may exit the canal 10 by a small length or may end at the periphery of the entry to the canal 10. The remaining section of the string 6, in any event, should be easily accessible by hand, tweezers, forceps, or other simple grasping mechanism without penetrating deep within the canal 10.

The porous media 4 is removable from the canal 10 via the string 6. In removal of the porous media 4, the string 6 is grasped at the end nearest the exit of the canal 10. The string 6 is then pulled in a direction extending outward from the canal 10. As the string 6 is pulled, the porous media 4, being attached to the string 6, is also pulled. Movement of the string 6 moves the porous media 4, therefore, as the string 6 is pulled from the canal 10, the porous media 4 follows. The porous media 4 and string 6 are in this manner removed from the ear 9.

The porous media may be coated, soaked, immersed, or otherwise impregnated with one or more therapeutic agents. The therapeutic agents may be a wide variety of chemicals, medications, substances, and the like.

When the porous media 4 is located in place within the external auditory canal 10 of the ear 9, the porous media 4 is in direct contact with the lining of the canal 10. In that location, the porous media 4 may serve to apply therapeutic agents to the lining of the canal 10. Furthermore, the porous media 4 may directly contact the tympanic membrane 4.

In these contacts of the porous media 4 with the ear 9, therapeutic agents from the porous media 4 can penetrate through the tympanic membrane 4 to affect the middle ear 14, which houses the delicate auditory ossicles (malleus, incus and stapes) and where fluid accumulates in otitis media with effusion (glue ear). Furthermore, therapeutic agents from the porous media 4 could penetrate to the inner ear 18, which houses the delicate semicircular canals that help the body maintain its balance. Therapeutic agents can also penetrate to the eustachian tube 16 which runs from the middle ear 14 to the back of the nose. The eustachian tube 16 is the only opening through which air enters the middle ear 14. Children are more susceptible to middle ear 14 infections than adults because children have shorter eustachian tubes 16 that make it easier for bacteria and viruses from the nose and throat to reach the middle ear 14. Even more, the porous media 4, when placed in the proximal aspect of the external auditory canal 10, is advantageously positioned to deliver therapeutic agents to the tympanic cavity, which includes the ear drum 12, carotid artery (not shown), internal jugular vein (not shown), facial nerve (not shown), middle ear 14, inner ear 18, and the eustachian tube 16.

Medications used to treat otitis media and otitis externa (swimmer's ear) often require regular controlled doses of therapeutic agents applied over an extended period of time. Oral tablets or suspensions of drugs require large doses to overcome the destructive effects of gastric acids and are eventually diluted throughout the entire body. The systemic effects of such large doses in infants and children can result in allergic or anaphylactic reactions. Intramuscular injections are traumatic and can result in nerve injury and sterile abscesses. Direct application of the medications to the pathological site is desired since the dosage is smaller and the effect immediate. The therapeutic applicator 2 allows a controlled dosage of therapeutic agents to be administered via the porous media 4 for a desired period of time. Treatment can be immediately discontinued by removal of the porous media 4 from the external auditory canal 10.

The advantages of delivering the medications and agents directly to the ear canal 10, tympanic membrane 12, middle ear 14 and eustachian tube 16 are readily apparent. During swallowing, the eustachian tube 16 is opened and air is admitted into the tympanic cavity (not shown), allowing atmospheric pressure to be kept equal on both sides of the ear drum 12. Medications and agents applied to the tympanic cavity have direct access to the carotid artery, internal jugular vein, facial nerve and internal structures of the ear.

Penetration enhancing substances allow the infiltration of medications and chemical agents through the membranes and lining of the ear canal 10. Penetration enhancers can be enzymatic or non-enzymatic. Non-enzymatic penetration enhancers facilitate infiltration of biologically active agents, such as medications and chemical substances, through the membranes and lining of the ear canal 10.

Penetration enhancers may have a variety of compositions. Such compositions include but are not limited to alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO) and methyl dodecyl sulfoxide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; and admixtures thereof.

A small amount of a local anesthetic, such as benzocaine, can be provided to the porous media 4 in order to alleviate pain and discomfort.

If cerumen is noted obstructing the ear canal, a cerumenolytic solution may be applied to the ear canal and the wax and debris removed with a curet or with the porous media 4 impregnated with the cerumenolytic solution, prior to insertion of the porous media 4 impregnated with medications. The porous media 4 may, in certain embodiments for such applications, be fastened to the hollow tube 8 by means of an adhesive. The porous media 4 may then be used to remove cerumen and debris prior to insertion of the porous media 4 containing therapeutic agents, or for the removal of macerated tissue from the ear canal 10 as found in otitis externa (swimmer's ear). The porous media 4, shown in FIG. 5, is especially suitable for use for this removal. Examples of medical treatment for swimmer's ear include: hydrogen peroxide, isopropyl alcohol, aluminum acetate solution, boric acid, antibiotics, and steroids. Examples of medical treatment for the removal of cerumen from the ear canal include: thonzonium bromide, 2% acetic acid, triethanolamine polypeptide oleate, 6.5% carbamide peroxide, alcohol, anhydrous glycerin, and a topical anesthetic such as benzocaine. These agents, or combinations thereof, may be impregnated in the porous media 4 of the therapeutic applicator 2 prior to and/or after insertion of the porous media 4 into the ear canal 10.

One method of making the porous media 4 for use in treatment is to supply the therapeutic applicator 2 in a sterile container and then apply therapeutic agents to the porous media 4 prior to insertion of the porous media 4 into the ear canal 10. Another method is to provide a prepared solution with a dropper top so that the porous media 4 can be impregnated with the prepared solution prior to insertion and also after the porous media 4 is in place within the canal 10. In such instance, solution can be provided into the ear canal and absorbed and maintained in contact with the ear canal 10, tympanic membrane 12 and other sites by the porous media 4. A combination solution of antibacterial, antifungal, anti-inflammatory and drying agents, with a local anesthetic, pH regulator and permeation enhancers could be provided for immediate use.

It will be appreciated by those skilled in the art, having the benefit of this disclosure, that this invention is capable of insertion into the ears and other body cavities of humans and animals. Furthermore, it is also to be understood that the form of the invention shown and described is to be taken as presently preferred embodiments. Various modifications and changes may be made without departing from the spirit and scope of the invention as set forth in the claims.

What is claimed is:

1. A therapeutic applicator for treating an aural canal, consisting of:

a) a hollow tube, having a first end, a second end, and a first cross-section;

b) a porous media, slightly larger than the first cross-section of the hollow tube and located outside of the hollow tube at the second end, such that the porous media covers the second end of the hollow tube so that the second end is substantially unexposed; and wherein the porous media has a central longitudinal axis; and b) a string attached to the porous media;

wherein the string enters into the hollow tube through the second end, passes through the hollow tube, and exits the hollow tube at the first end when the porous media is located at the second end; and wherein said string is attached to said porous media in a manner such that when a tension force is applied to the string the tension force is centered along said central longitudinal axis of the porous media; and wherein the hollow tube is employed to push the porous media into the aural canal and withdrawn once the porous media is so positioned, so that the porous media remains in the aural canal and the string passes within and outside the aural canal when the hollow tube has been withdrawn; and wherein the porous media located outside of the hollow tube at the second end prior to withdrawal of the hollow tube provides protection from injury by the second end of the hollow tube when pushing the porous media via the hollow tube into the aural canal.

2. A therapeutic applicator for treating an aural canal, consisting of:

a) a hollow tube, having a first end, a second end, and a first cross-section;

b) a porous media, slightly larger than the first cross-section of the hollow tube and located outside of the hollow tube at the second end, such that the porous media covers the second end of the hollow tube so that the second end is substantially unexposed; wherein a therapeutic agent is impregnated in the porous media and wherein the porous media has a central longitudinal axis; and b) a string attached to the porous media;

wherein the string enters into the hollow tube through the second ends passes through the hollow tube, and exits the hollow tube a the first end when the porous media is located at the second end; and wherein said string is attached to said porous media in a manner such that when a tension force is applied to the string tension force is centered along said central longitudinal axis of the porous media; and wherein the hollow tube is employed to push the porous media into the aural canal and withdrawn once the porous media is so positioned, so that the porous media remains in the aural canal and the string passes within and outside the aural canal when the hollow tube has been withdrawn; and wherein the porous media located outside of the hollow tube at the second end prior to withdrawal of the hollow tube provides protection from injury by the second end of the hollow tube when pushing the porous media via the hollow tube into the aural canal.

3. The therapeutic applicator of claim 1, wherein the porous media is generally spherical-shaped.

4. The therapeutic applicator of claim 1, wherein the porous media is generally cylindrical-shaped.

5. The therapeutic applicator of claim 1, wherein the porous media is generally conical-shaped.

6. The therapeutic applicator of claim 2, wherein the therapeutic agent is selected from the group consisting of an antibiotic, an anti-inflammatory, an antifungal agent, a drying agent, and a combination thereof.

7. The therapeutic applicator of claim 2, wherein the therapeutic agent is selected from the group consisting of a pH modifying agent, a permeation enhancer, an anesthetic, and a combination thereof.

8. The therapeutic applicator of claim 2, wherein the therapeutic agent is selected from the group consisting of an antibiotic, a steroid, hydrogen peroxide, isopropyl alcohol, boric acid, aluminum acetate solution, thonzonium bromide, triethanolamine polypeptide oleate, carbamide peroxide, anhydrous glycerin, benzocaine, and a combination thereof.

9. The therapeutic applicator of claim 1, wherein the porous media has a generally diametrical hole and the string extends through the diametrical hole of the porous media and is joined after passing through the porous media.

10. The therapeutic applicator of claim 1, wherein the string extends more than once through the porous media and is joined after passing through the porous media.

11. A method for applying treatment to an aural canal, comprising the steps of:

attaching a porous media to a string;

threading the string through a hollow tube of slightly smaller cross-section than the porous media, so that the porous media is located at and substantially covers a first end of the hollow tube and the string passes through the hollow tube and exits a second end of the hollow tube;

placing the porous media at an entry to the aural canal;

pushing the porous media into the aural canal via the hollow tubes; and withdrawing the hollow tube from the aural canal so that the porous media remains in the aural canal and the string passes from attachment with the porous media, through the aural canal, and out of the aural canal at the entry.

12. The method of claim 11, further comprising the step of:

attaching a string to the porous media prior to the step of pushing;

wherein the string remains accessible without entry into the body cavity.

13. The method of claim 12, further comprising the step of:

pulling the string away from the body cavity;

wherein the step of pulling removes the porous media from within the body cavity.

* * * * *